US012746336B2

(12) United States Patent
Boström

(10) Patent No.: US 12,746,336 B2
(45) Date of Patent: Sep. 29, 2026

(54) SUPPORT STRUCTURE, MEDICAMENT DELIVERY DEVICE AND METHOD OF ASSEMBLYING

(71) Applicant: SHL MEDICAL AG, Zug (CH)

(72) Inventor: Anders Boström, Ingarö (SE)

(73) Assignee: SHL Medical AG, Zug (CH)

( * ) Notice: Subject to any disclaimer, the term of this patent is extended or adjusted under 35 U.S.C. 154(b) by 929 days.

(21) Appl. No.: 17/611,856

(22) PCT Filed: Jun. 25, 2020

(86) PCT No.: PCT/EP2020/067767
§ 371 (c)(1),
(2) Date: Nov. 16, 2021

(87) PCT Pub. No.: WO2021/008839
PCT Pub. Date: Jan. 21, 2021

(65) Prior Publication Data
US 2022/0226577 A1 Jul. 21, 2022

Related U.S. Application Data

(60) Provisional application No. 62/875,724, filed on Jul. 18, 2019.

(30) Foreign Application Priority Data

Sep. 6, 2019 (EP) .................................... 19195869

(51) Int. Cl.
*A61M 5/24* (2006.01)
*A61M 5/20* (2006.01)
(Continued)

(52) U.S. Cl.
CPC ........ *A61M 5/2422* (2013.01); *A61M 5/2033* (2013.01); *A61M 5/31585* (2013.01);
(Continued)

(58) Field of Classification Search
CPC .............. A61M 5/2422; A61M 5/2033; A61M 5/31585; A61M 5/3204;
(Continued)

(56) References Cited

U.S. PATENT DOCUMENTS

2013/0041327 A1* 2/2013 Daniel .................... A61M 5/20 604/228
2019/0201612 A1* 7/2019 Klintenstedt ........... A61M 5/24

FOREIGN PATENT DOCUMENTS

KR 2018-0045062 A 5/2018
WO 2016/120207 A1 8/2016
(Continued)

OTHER PUBLICATIONS

International Search Report and Written Opinion for Int. App. No. PCT/EP2020/067767, mailed Sep. 1, 2020.

*Primary Examiner* — Chelsea E Stinson
*Assistant Examiner* — Hamza A Darb
(74) *Attorney, Agent, or Firm* — McDonnell Boehnen Hulbert & Berghoff LLP

(57) ABSTRACT

The present disclosure relates to a support structure for a medicament container used in a medicament delivery device. The support structure accommodates an elongated plunger rod and a drive spring and can have a tubular body having a predetermined radial dimension, a longitudinal axis (A), a distal end and a proximal end and at least one first flexible element arranged at the proximal end of the tubular body and having the same radial outer and inner dimensions as the tubular body. The flexible element is provided with a contact member with an outer radial dimension extending the outer dimension of the tubular body for compensating of manufacturing tolerances of the medicament containers made of glass.

20 Claims, 6 Drawing Sheets

(51) Int. Cl.
*A61M 5/315* (2006.01)
*A61M 5/32* (2006.01)

(52) U.S. Cl.
CPC ... *A61M 5/3204* (2013.01); *A61M 2005/2013* (2013.01); *A61M 2207/00* (2013.01)

(58) Field of Classification Search
CPC ...... A61M 2005/2013; A61M 2207/00; A61M 2005/2418; A61M 2005/2477; A61M 2005/3267; A61M 2205/581; A61M 2205/582; A61M 2205/583; A61M 5/24; A61M 5/20; A61M 5/3157; A61M 5/326
See application file for complete search history.

(56) References Cited

FOREIGN PATENT DOCUMENTS

| | | | |
|---|---|---|---|
| WO | 2016/193355 | A1 | 12/2016 |
| WO | 2017/191159 | A1 | 11/2017 |
| WO | 2019/137701 | A1 | 7/2019 |

* cited by examiner

SUPPORT STRUCTURE, MEDICAMENT DELIVERY DEVICE AND METHOD OF ASSEMBLYING

CROSS REFERENCE TO RELATED APPLICATIONS

The present application is a U.S. National Phase Application pursuant to 35 U.S.C. § 371 of International Application No. PCT/EP2020/067767 filed Jun. 25, 2020, which claims priority to U.S. Provisional Patent Application No. 62/875,724 filed Jul. 18, 2019 and European Patent Application No. 19195869.3, filed Sep. 6, 2019. The entire disclosure contents of these applications are herewith incorporated by reference into the present application.

TECHNICAL FIELD

The present application relates to a support structure for a medicament container for holding the medicament container in a steady state inside a medicament delivery device.

BACKGROUND

Many medicament delivery devices are developed for self-administration, i.e. a user performs the medicament delivery her-, or himself. This requires a medicament delivery device, which is as safe to use and as easy to handle as possible. In order to meet these requirements, the risk of human errors must be minimized, the number of actions needed to be performed in order to receive a dose shall be reduced, and the device must be intuitive and ergonomic to use. Thus, in order to minimize the risk of human errors, it is desirable to have the device as pre-assembled for a deliver to the user.

An important aspect of automatic injectors is a human aspect of handling the injector regarding how it is held during penetration, a general aim is to have the patient holding the injector in an ergonomic way that may permit the penetration and injection in different locations on the body, such as around the waist and also on the backside of the waist and/or in the buttocks of the patient. Sometimes the patient does not see the injector at those locations and need to be able to hold the injector without having to change grip. By removing the action of pushing a button or making them automatically fired, the patient is free to hold the device as he desires and feels comfortable.

It is considered important for the patient to receive a confirmation that the injection has been made, in particular in instances when an injector is used where the patient does not see the injector, e.g. such as around the waist and also on the backside of the waist and/or in the buttocks of the patient. In order to prevent accidental injuries after a completed injection, it is desired e.g. to lock a needle guard in an extended position safely covering a sharp injection needle.

There are many different devices had been developed in the last years, such as automatic injectors. On the other hand, there are manufacturing tolerances when components of the automatic injector are manufactured and assembled. It is a known problem that the automatic medicament delivery devices such as e.g. automatic injectors often comprise a medicament container or a prefilled syringe made of glass. It is known in the art that those glass syringes have manufacturing tolerances in their dimensions, which may cause different problems during assembly or use of the medicament delivery device.

Document W2017/191159 A1 discloses a powerpack to be used with a medicament delivery device, which power pack comprises a plunger rod and is characterized in signal initiating elements for providing information to a user of a medicament delivery device about the movement of said plunger rod, when the plunger rod sleeve has been activated to release holding elements.

Document US 2019/201612 A1 discloses an intermediate structure for a support structure to cooperate with a medicament container, comprising a flexible element arranged to exert a force on a distal end surface of said medicament container, wherein said intermediate structure is arranged between said flexible element in an outwardly direction in relation to a longitudinal axis when exerting a force on said medicament container.

Document WO2016/193355A1 discloses a syringe support for an autoinjector. The syringe support has a couple of bellow-shaped flexible portions for absorbing of the length variations of the syringe made of glass.

Document WO2016/120207A1 discloses an automatic medicament delivery device having a pair of arch-shaped flexible elements on a distal end of a tubular component of a drive unit. The pair of flexible elements are made for compensating of syringes length variations as they face a flange of a glass syringes to urge it forward during the assembly. This allows avoid the syringe rattling into the housing due to different length of the glass syringes and thus a breakage during a transportation and/or activation of the automatic medicament delivery device.

On the other hand, the glass syringes have not only length tolerances, but also a radial dimensions' variation. Therefore, it is not excluded that the flexible elements might be flexed inwardly into the syringe interior and lead to a jam and breakage.

Document WO2019/137701A1 discloses a support structure for an automatic medicament delivery device aiming to solve this problem with undesired flexing of a length tolerance compensating elements during a contact with a syringe flange. The flexible elements in form of arched wings at a proximal end of the support structure. The flexible wings are supposed to flexibly urge the syringe in a proximal direction during assembly and/or activation for avoiding its rattling due to manufacturing tolerances. Each flexible wing is provided with an inwardly directed protrusion of a particular shape to ensure the flexing of the supporting flexible elements outwards. A drawback of this solution is an increased friction between a plunger rod surface during its proximal movement and the support structure flexible wings. Therefore, there is a need to avoid rattling of the syringe due to its urging in proximal direction and the same time do not negatively impact functionality.

It is also known, that manufacturing tolerance of the glass containers and glass syringes appears not only in length but also in radial dimensions. This means that the e.g. a syringe distal flanges can have a different radius between the flange surface and the syringe interior or inner chamber, thus different diameters of the syringe distal opening. Therefore, in the case of the syringe with the larger distal opening to be inserted into the automatic injector, the flexible elements for length variation compensation might be lead to flex into this opening instead of flexing outwards. Therefore, there is a need to solve this problem, and to achieve a component compensating for both, radial and length variations in size for glass components.

SUMMARY

The object of the present disclosure is to provide a medicament delivery device that is reliable and easy to use when handling and activating and easy to assembly. This is achieved by an automatic medicament delivery device with an elongated housing having a proximal end and a distal end. A medicament container is to be accommodated into the housing. The medicament container is equipped with a medicament delivery member on a proximal end and a distal end flange. A plunger rod, when released, acts on a stopper inserted in the distal end of the medicament container for start of a medicament delivery. The plunger rod is driven by a drive spring and accommodated in a support structure. The support structure supports on its outer surface a rotational member interacting with the support structure for locking and releasing of the plunger rod axial movement when the rotational member rotates. An axially movable activator for activating the medicament delivery device is inserted into the housing for interacting with the rotational member. The rotation of the rotational member releases the plunger rod axial movement in the proximal direction and locks the actuator after completion of the medicament delivery. The medicament delivery device comprising the tubular support structure having the at least one first flexible element extended in a proximal direction, provided on its outer surface with a contact member. The outer radial of the contact element dimension extends over the first flexible element outer dimension and is arranged to contact a distal end flange of the medicament container or the syringe preventing the flexing of the flexible element inwardly into the syringe interior.

According to a further aspect of the disclosure, to ensure that the due to manufacturing tolerances in length and in diameters of the glass container, the medicament delivery device functioning properly, an elongated support structure is used for supporting axially a distal end flange of a medicament container to be inserted into a medicament delivery device. The support comprises a tubular body having an inner dimension and an outer dimension, a longitudinal axis. The tubular body has a distal end and a proximal end. At least one first flexible element is arranged at the proximal end of the tubular body extending in a proximal direction and facing the medical container distal end. The at least one flexible element has the same outer dimension (and the same inner dimension as the tubular body. The at least one first flexible element is provided on its outer surface with a contact member which has an outer radial dimension extending over the first flexible element outer dimension and which is arranged to contact the distal end flange of the medicament container.

According to another aspect of the disclosure, the at least one first flexible element the support structure comprises a first front surface inclined in relation to the longitudinal axis and facing in the proximal direction.

According to a yet another aspect of the disclosure, the contact member comprises a second front surface extending radially in an inclined direction in relation to the longitudinal axis over the first front surface of the flexible element and facing in the proximal direction. The first surface of the flexible element and the second surface of the contact member are situated at the same angle in relation to the longitudinal axis.

According to a yet a further aspect of the disclosure, the first surface and the second surface are inclined at the different angles to the longitudinal axis.

According to another aspect of the disclosure, the first flexible element is able to flex radially only outwardly relative to the axis when brought in contact with the medicament container distal end surface of flange due to an increased total radial contact surface of the flexible element and the contact member which covers possible diameter variations of the glass syringes.

According to a further aspect of the disclosure the support structure further comprises a second flexible element identical in shape and dimension to the first flexible element, which extends symmetrically in the longitudinal axis direction from the tubular support structure proximal end and diametrically opposite to the first flexible element.

According to yet another aspect of the disclosure the contact member has one of a rectangular and a semi-spherical shape which is to be fit into a corresponding recess on an inner surface of the rotational member.

According to yet a further aspect of the disclosure, a drive mechanism or a second sub-assembly is used for activating an elongated medicament delivery device having a longitudinal axis and a medicament container such as a syringe with a proximal end and a distal end. The container is to be inserted into the medicament delivery device. The drive mechanism comprises a plunger rod for acting on the medicament container for delivery of a medicament within a pre-filled container. A pre-tensioned drive spring is inserted into the tubular hollow plunger rod for moving the plunger rod in the proximal direction when the plunger rod is being released for movement. A support structure accommodates the plunger rod with the drive spring inside and supports on its outer surface a rotational member interacting with the support structure for locking and releasing of the plunger rod. An activator is movable axially in a distal direction for interaction with the rotational member for its rotating; releasing the locked plunger rod with an inserted pre-tensioned driving spring and activation of the medicament delivery due a distal movement of the plunger rod urged by the pre-tensioned spring.

By the term automatic medicament delivery device, is herein meant a medicament delivery device adapted to deliver a medicament without a user having to press a push button or activation member, but instead only by pressing the proximal end of the medicament delivery device against the delivery site.

According to another aspect of the disclosure, a distal end of the tubular forms a distal end of the medicament delivery device. The tubular structure in inserted in the distal end of the medicament delivery device housing.

The medicament delivery device further comprising a medicament delivery member, e.g. such as an injection needle. The axially movable activator is a medicament delivery member guard to be pressed against an injection site. The medicament delivery guard comprises a guard spring biasing the medicament delivery guard in an extended position from the proximal end of the housing, when the guard spring is being released. A protective cap at the proximal end of the medicament delivery housing is attached to the activator and protecting the medicament delivery member due to friction.

According to yet another aspect of the disclosure, the medicament delivery device is an auto-injector and the medicament delivery member is an injection needle. The protective cap comprises a needle shield remover for removal of the needle shield form the needle simultaneously upon removal of the protective cap and thus releasing the medicament delivery member guard for proximal axial movement to the extended position. The medicament delivery device is an auto-injector, e.g. a single-dose disposable injector.

The medicament delivery device according to the present disclosure presents a number of advantages. There is a high degree of functionality and automation, which remove unnecessary components and actions for delivering a medicament.

Also an important safety aspect is met since, during withdrawal from the injection site, the tubular activation member is pushed out and covers the delivery member e.g. a needle, and also is been locked in the extended state, thereby preventing unintentional needle sticks. Furthermore, the extended radially outwards contact members of the flexible arch-shaped wings at the proximal end of the support structure provide increased the support surface for contact with the syringe flange. Thus, a compensation of the manufacturing dimensions', the variations both in length and in the inner diameter of the syringe, is achieved, rattling of the syringe is prevented and the flexible wings are able to flex only outwardly relative to a central axis.

According to yet another aspect of the disclosure, a method of assembling the medicament delivery device includes assembling two sub-assemblies of a proximal end and a distal end of the device. The method comprises steps of inserting a medicament delivery member shield remover into a protective cap, inserting a spring for an activator and the activator into a central axial opening of a housing from a proximal end and putting a protective cap onto the activator proximal end thus forming a first sub-assembly.

The method further comprises steps of inserting of a drive spring into a plunger rod and those together into a support structure central axial opening. The support structure has a tubular body and at least one first flexible element arranged at a proximal end of the tubular body. A rotational member is placed onto the support structure. Rotating of the rotational member about the axis is locking the drive mechanism components together thus forming a second sub-assembly. On the at least first flexible element is provided a contact member with a proximal surface extending in a radial direction over a contact surface of the first flexible element and arranged to contact a distal end of a pre-filled medicament container, when inserted between the first and the second sub-assemblies and ensuring that the flexible element is flexing only outwards relative to the axis A due to an enlarged total contact surface of the first flexible element and the contact member.

According to yet a further aspect of the disclosure, the method of assembly of the medicament delivery device has a further step of inserting a pre-filled medicament container into the first sub-assembly of the medicament delivery device from a distal end of the housing and inserting the assembled drive mechanism as the second sub-assembly thereafter from the distal end into the housing. An at least one first flexible element contacts the distal end or distal flange of the inserted pre-filled medicament container preventing its axial movement after the assembly.

These and other aspects of and advantages with the present disclosure will become apparent from the following detailed description and from the accompanying drawings.

BRIEF DESCRIPTION OF THE DRAWINGS

In the following detailed description of the disclosure, reference will be made to the accompanying drawings, of which

DETAILED DESCRIPTION

In the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

Figure 1:
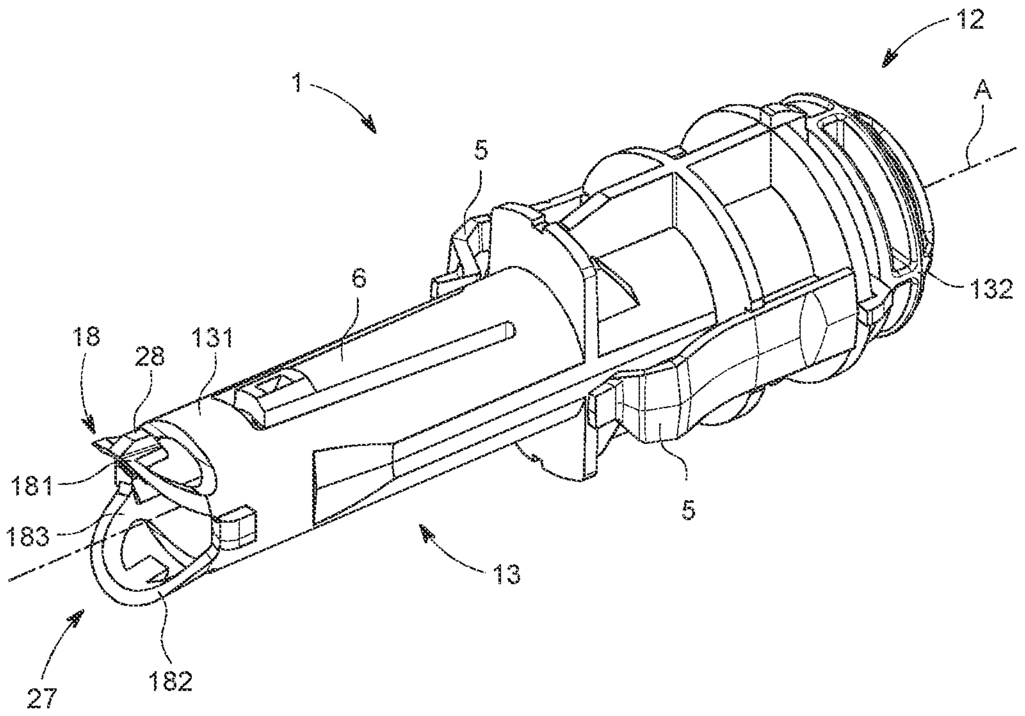
FIG. 1 shows a perspective view of a first embodiment of an internal support structure of the medicament delivery device.
Figure 2:
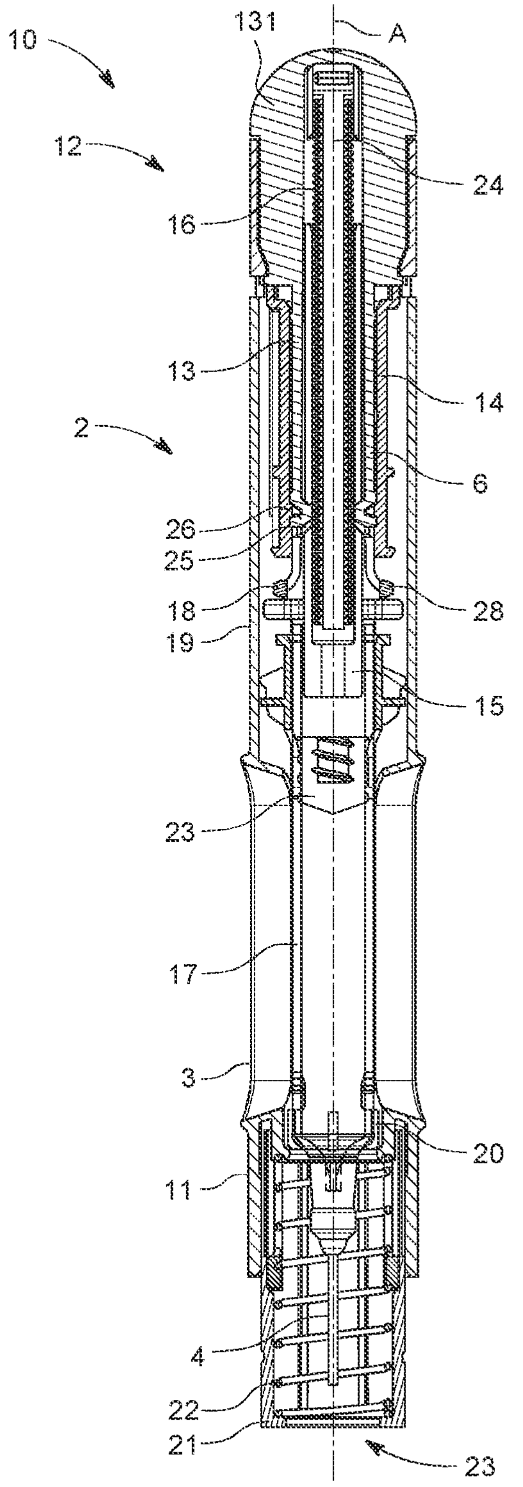
FIG. 2 shows a longitudinal cross-section of a first embodiment of an elongated medicament delivery device with an inserted syringe.

FIG. 1 illustrates, in perspective, a tubular support structure 1 is inserted into an elongated housing 3 of an exemplary medicament delivery device 10 as shown in FIG. 2. The tubular housing 3 has a proximal end 11 and an opposite distal end 12. The tubular support structure 1 further comprises a tubular body 13. The support structure 1 has a proximal end 131 and a distal end 132 along a central axis A. The distal end 132 of the support structure 1 has a larger dimension relative to the proximal end 131 and provided with a pair of flexible arms 5 extending in a proximal direction along the axis A, able to flex from and to the axis A and situated one opposite the other diametrically. In some embodiments, the distal end 132 of the support structure 1 forms a distal end 12 of the medicament delivery device 10 of this embodiment. The tubular body 13 is equipped with a pair of flexible arms 6 extending in a proximal direction along the axis A, able to flex from and to the axis A and situated one opposite the other diametrically. The flexible arms 6 of the tubular body 13 are displaced on 90° relative to the flexible arms 5 of the distal end 132. The tubular body 13 has a central opening 27 on its distal end for insertion of some components during assembly of the medicament delivery device 10. The proximal end 131 of the tubular body 13 is provided with a pair of flexible elements 18, which is here e.g. an arch-shaped wings 18 extending from the tubular body 13 edge in a proximal direction parallel to the axis A one opposite the other and made integrally with the tubular body 13 by e.g. a precision moulding. Alternatively, the only one flexible element 18 in the other configuration can be used and it might be a separate component.

Figure 10:
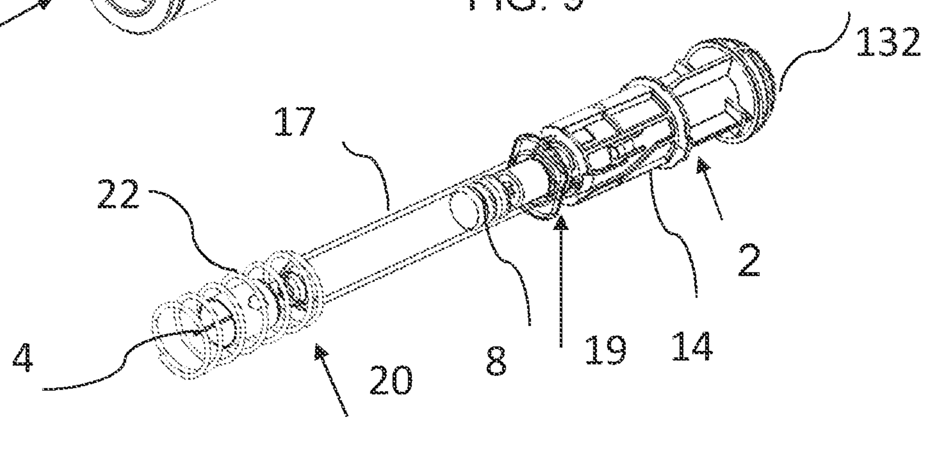
FIG. 10 illustrates a partial perspective view of some components included in a drive mechanism such as the rotation member placed on the support structure outer surface, an inserted into the support structure plunger rod, which is shown partly inside a syringe and in a contact with a stopper on the syringe distal end. A needle is mounted on a proximal syringe end of the syringe and surrounded by a spiral metal spring of a needle guard.

Each flexible element 18 is defined by an outer surface 181, having the same radial dimension "D" as the rest of the tubular body 13; an inner surface 183, having the same radial dimension "d" as the interior of the tubular body 13, and an inclined in relation to the axis A front surface. The flexible elements 18 are supposed to support a distal end 19 or a flange 19 of a prefilled medicament container 17, e.g. a syringe 17 in this embodiment (as also illustrated in FIG. 10). The flexible elements 18 are able to flex radially outwardly from the axis A, when getting in a contact with the syringe 17 distal end 19, if the syringe 17 length is a bit longer. It is known that a manufacturing length variation can be of about 3-5% of the length, that might be of about +/−1.5 to 2.5 mm for the syringes of 50 mm. During assembly for ensuring of the syringe 17 firm fixation into the medicament delivery device 10 without movability in axial direction A, the flexible elements 18 are urging it forward and due to their flexibility/deformation provide a necessary compensation for manufacturing tolerances of the pre-filled medicament container 17 or the syringe 17. The flexibility of the elements 18 allows avoiding rattling and possible damage of the glass syringe container 17, which is fragile. The tubular support 1 with the flexible elements 18 allows assembling of syringes with varying lengths due to manufacturing tolerances within the same housing without any gaps between the neighbouring components in axial direction.

At the arch-shaped element 18 highest point, in the middle of each arch-shaped flexible wing 18, a contact member 28 is situated on an outer surface 181 of the flexible element 18; the outer surface 181 faces away from the axis A. In this exemplary embodiment of FIG. 1, there are two opposite each other flexible elements 18, and each flexible element or flexible wing 18 is equipped with the contact member 28 extending radially from the flexible element 18 outer surface 181 and thus enlarging a contact area of the wings 18 with the oppositely situated syringe 17 distal end with a central opening and a flange 19. This enlarged contact area of the flexible element 18 is able to compensate for a diameter variation for the glass syringe 17 central opening. This means that, if the central opening of the syringe 17 is somewhat larger, the proximal surface 29 of the contact member 28 extending radially over the dimension "D" of the proximal end 131 of the tubular body 13 (see FIG. 4) would ensure contact of the flexible elements 18 in form of wings 18 in this embodiment with the distal end 19 and/or the flange 19 of the syringe 17 and would prevent the flexible elements 18 to flex inwardly and/or be led into the syringe 17 central opening.

Figure 8:
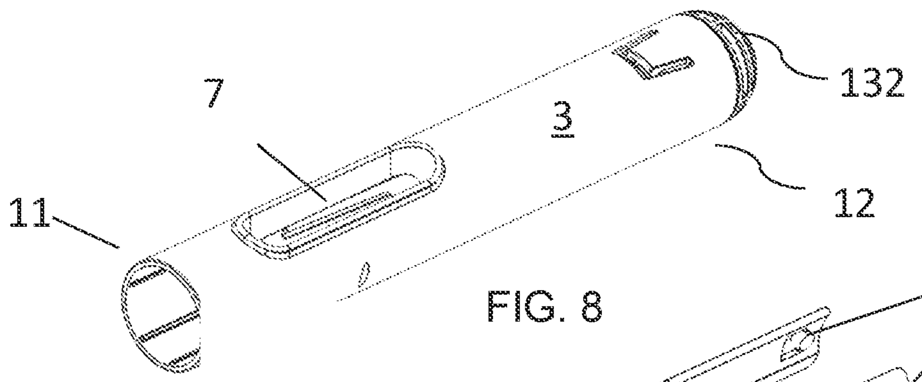
FIG. 8 illustrates a tubular housing of the medicament delivery device with a monitoring window and inner ribs along the housing for guiding an activator longitudinal movement.
Figure 13:
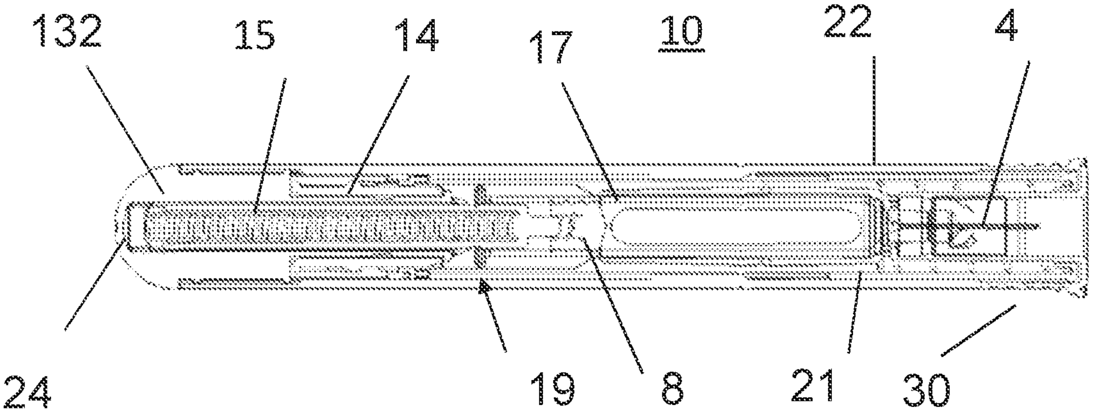
FIG. 13 illustrates a cross-sectional along the longitudinal axis of the medicament delivery device longitudinal view with a protective cap satiated onto the activator in a state prior to activation of the medicament delivery device.
Figure 14:
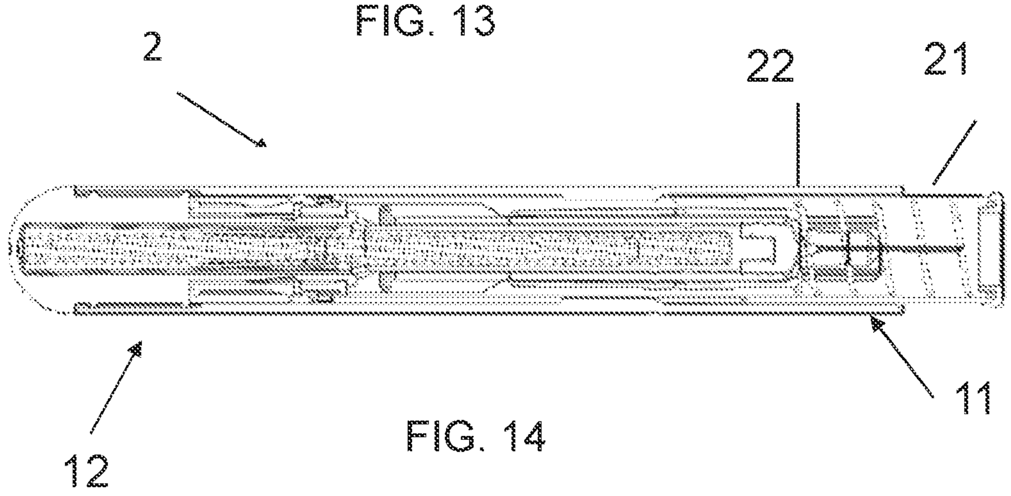
FIG. 14 illustrates a cross-sectional along the longitudinal axis of the medicament delivery device longitudinal view in a state after an injection has been completed.

FIG. 2 illustrates schematically the assembled medicament injection device 10 with a removed protective cap 30 (see FIG. 121 and FIG. 13) prior to start of the injection. A drive mechanism 2 is situated in the distal end 12 of the housing 3. The drive mechanism 2 comprises among others the tubular support structure 1 having the tubular body 13, a tubular hollow plunger rod 15 accommodating a first resilient member 16 in form of a drive spring 16 and been inserted into the central opening 27 of the tubular body 13, and a rotational member 14 situated onto the outer circumferential surface 133 of the tubular body 13. The first drive spring 16 might be placed around a metal support rod 24. The tubular body 13 is provided with a pair of flexible elements 18 in form of two arch-shaped wings 18. The flexible elements 18 are able to flex outwards relative to the central axis A so as to bias a syringe 17 via its distal end flange 19 in the proximal direction until its proximal end 20 is set firmly on a seat formed on an interior of the housing 3 proximal end 11. The plunger rod 15 is arranged to move forward in the proximal direction a stopper 8 when conducting an injection. The movement of the stopper 8 can be observed thought a monitoring window 7 (as illustrated in FIG. 8) or two windows in the housing 3. The proximal end 20 of the glass syringe 17 is equipped with a medicament delivery member 4 which is in this embodiment is an injection needle 4. The needle 4 is usually protected by a needle cover (not illustrated here) and surrounded by a delivery member guard 21. In this embodiment, the needle guard 21 functions as an activator 21 for the medicament delivery device 10. The activator 21 is provided with a needle guard spring 22 biasing the activator 21 in a form of the needle guard 21 in the proximal direction to an extended position as illustrated in FIG. 2.

Figure 3:
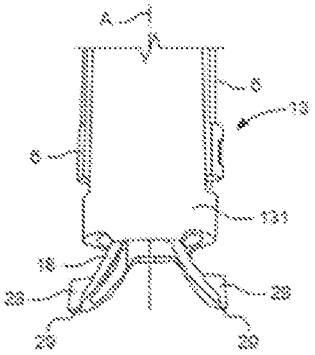
FIG. 3 illustrates a partial view of a tubular body of the support structure with a pair of flexible elements having contact members of a first embodiment.

As disclosed previously, the flexible elements 18 are provided with the contact members 28. FIG. 3 illustrates a first embodiment of the contact member 28. The contact member of this embodiment has a rectangular shape and its front surface 29 facing a proximal direction is perpendicular to the axis A. The shape of the contact member 28 is adapted to be received and guided by a corresponding recess on the inner surface of the tubular rotational member 14 (visible in FIG. 7). When the rotational member 14 is to be assembled onto the tubular body 13, the flexible elements 18 are guided by the contact members 28 sliding in the recesses to flex inwardly and thus to be put onto the tubular body 13 from its proximal end 131. The two partially shown flexible elongated arms 6 of the tubular body 13 are situated one the opposite the other on the tubular body 13 circumference 133.

Figure 4:
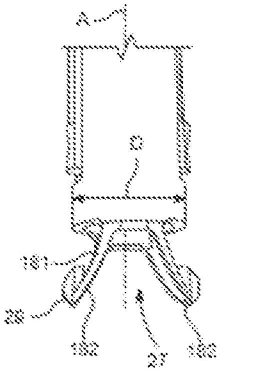
FIG. 4 illustrates a partial view of a tubular body of the support structure with a pair of flexible elements having contact members of a second embodiment.

FIG. 4 illustrates a second embodiment of the contact member 28, which has a trapezoidal shape, but might be a half-spherical shape (not shown) also. The front surface 28 in this case is inclined to the central axis S. The stop member 28 has a radial dimension that extends the radial dimension "D" of the proximal end 131 of the tubular body 13. The surface 182 of the first flexible element 18 in the pair of the elements 18 faces a situated opposite the similar surface 182 of the second flexible element 18 in the pair relative the axis A, both surfaces 182 face the proximal direction and both are inclined in relation to the central axis A at the same angle. The outer surfaces 181 of the flexible elements 18 are even with the outer circumference surface 133 of the tubular body 13 proximal end 131 and have the same radial dimension "D". The central opening 27 of the proximal end 131 of the body 13 has the inner diameter "d" which is equal to a dimension of or a distance between the inner surfaces 183 of the flexible elements 18.

Figure 5:
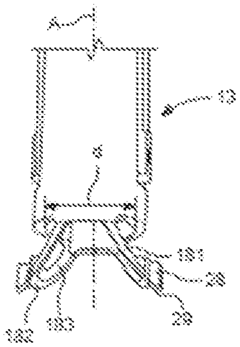
FIG. 5 shows a partial view of a tubular body of the support structure with a pair of flexible elements having contact members of a third embodiment.

FIG. 5 illustrates a third embodiment of the contact elements 28 having a proximal contact surface 29 even with the inclined surface 182 of the flexible elements 18 and inclined at the same angle as the surface 182. The contact elements 28 of the third embodiment extend radially and increase the total contact surface 182 of the flexible elements 18 with the distal end 19 of the syringe 17.

Figure 6:
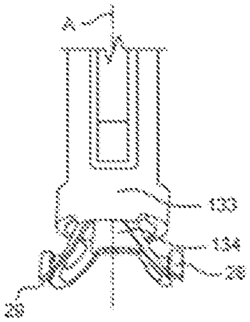
FIG. 6 shows a partial view of a tubular body of the support structure with a pair of flexible elements having contact members of a fourth embodiment.

FIG. 6 illustrates a fourth embodiment of the contact elements 28 with the frontal contact surfaces 29. An inner circumference 134 of the proximal end 131 has the dimension "d".

Figure 7:
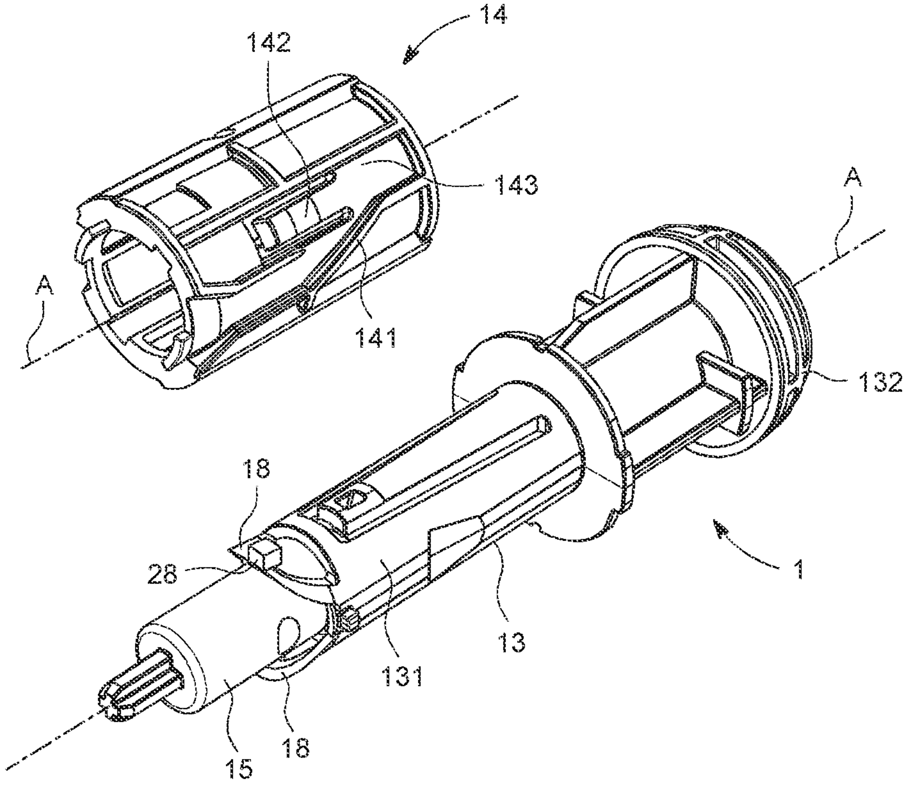
FIG. 7 shows a perspective view of the tubular support structure with an inserted plunger rod and a rotational member prior an assembling onto the support structure.
Figure 9:
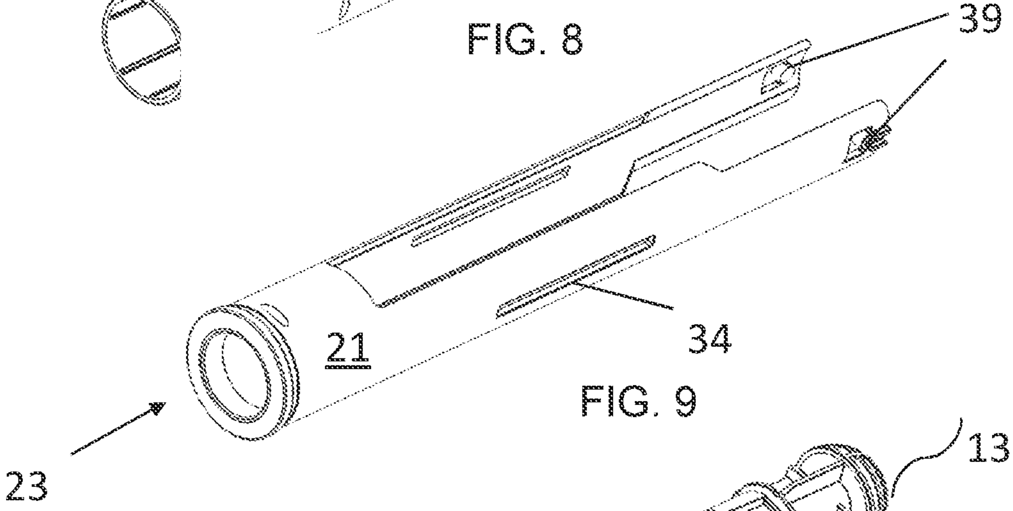
FIG. 9 shows a perspective view of the activator with a central opening and two guiding grooves along its longitudinal elongated arms.

FIG. 7 illustrates partially assembled the tubular support structure 1. The plunger rod 15 is inserted into the tubular body 13 of the support structure 1. The rotational member 14 been put onto the outer circumferential surface 133 of the tubular body 13 from its proximal end 131. The rotational member 14 has a pair of recesses in its inner surface interacting with and guiding the contact members 28 along the axis A during the assembly. The flexible elements 18 at the beginning of assembling are forced to flex inwardly until the contact members 28 run along the inner pair of the recesses, and when they run out of the rotational member 14, the flexible members 18 are able to flex outwardly. On the outer surface of the rotational member 14 a number of tracks 141, 143 are formed for interacting with at least one inwardly extending protrusion 39 (e.g. a pair of the radially inward projecting protrusions 39 as illustrated in FIG. 9 for this embodiment) on the distal end the activator 21. The radially inwards extending protrusion(s) 39 is(are) adapted to be guided within the at least one track 141, 143 forcing the tubular rotational member 14 to rotate when the tubular activator 21 is axially moved inside the medicament delivery device 10, when been pressed against an injection site. The radial protrusion 39 glides along the inclined track 141 into the straight portion of the straight track 143 turning the rotational member 14 along the central axis of about 35°. This movement releases the flexible arms 6 of the tubular body 13 allowing their flexing outwards, and thus the extensions 26 at the ends of the tubular body 13 arms 6, previously situated into the recesses 25 of the plunger rod 15, move out releasing the plunger rod 15, that is biased by the pre-tensioned drive spring 16, to move in the proximal direction. A pair of flexible tongues 142 of the rotational member 14 first allow the radial inwardly extending protrusions 39 to glide over due to flexing inwardly, and then, due to flexing outwardly in the initial position are locking the activator in form of the needle guard 21 in the extended position after the medicament delivery had been completed, preventing its movement in the distal direction.

FIG. 8 illustrates, in perspective, the tubular housing 3 of the exemplary medicament delivery device 10. The tubular housing 3 has a proximal end 11 and the opposite distal end 12 The tubular housing 3 further comprises at least one guiding protrusion or a rib on its inner surface of the wall, preferably two protrusions or two ribs symmetrically situated in relation to the central axis A. The protrusion or protrusions in form of ribs of the housing 3 is/are adapted to interact with at least one groove 34 of the activator 21 such as the tubular shaped needle guard 21 (e.g. as in FIG. 9), having preferably two symmetrical grooves 34. The groove 34 of the tubular activator 21 is used for locking the tubular activator 21 inside the tubular housing 3, when the tubular activator 21 is in its most proximal position, before and after an injection has been made. In an exemplary embodiment of FIG. 8, there are two guiding ribs, one on each side of the inner wall of the tubular housing 3. The two recesses 40 prevent rotation of the activator 21 when moved in the distal direction. The tubular housing 3 may further comprise a container holder (not illustrated here) which is coaxially arranged and fixedly attached within the tubular housing 3 for lodging the medicament container 17 (see FIG. 10). The medicament injection device 10 comprises the tubular support structure 1 forming the drive mechanism 2 as explained above, being coaxially arranged and fixedly attached to the distal end 12 of the housing 3.

FIG. 9 shows a central opening 23 in the activator 21 that has a dimension allowing a needle cover remover (which is not illustrated) usually been situated into the protective cap 30 to pass through the opening 23 when a needle cover (not shown) arranged on the injection needle 4 is to be removed. The needle cover in this embodiment is removed simultaneously with the removal of the protecting cap 30 from the activator 21 proximal end.

FIG. 10 illustrates a number of components in the interior of the medicament delivery device 10. The medicament delivery device 10 further comprises the second resilient member 22 or the second spring 22 is arranged in relation to the tubular activator 21 biasing it in the proximal direction from a non-activated position to an activated position. An annular proximal end of the activator 21 (as illustrated in FIG. 9) extends not more than about 1.9 mm from the proximal end 11 of the housing 3, when the medicament injection device 10 is in the non-activated state and whereby the annular proximal end of the activator 21 is extended at a predetermined distance, it might be of about 11-12 mm from the proximal end 11 of the housing 3, when the medicament injection device 10 is in an activated state.

The medicament container 17 might be arranged within the container holder (not shown) and has a predetermined volume of medicament, the slidable stopper 8 and the delivery member 4. In an exemplary embodiment of the present disclosure, the medicament container 17 is the syringe 17 provided with the needle 4 as the delivery member 4, however the present disclosure should not be limited to this. The other embodiments might include a medicament cartridge, one or multi-chamber cartridge, having a membrane on its proximal end, or the like where a delivery member can be adapted to penetrate the membrane for a delivery of the medicament.

The best seen in FIG. 10, the syringe 17 proximal end or flange 19 is urged axially in the proximal direction by the pair of flexible elements 18 of the tubular support structure 1 during assembly process for avoiding axial gaps and thus, avoiding a risk of the glass syringe breakage.

Figure 11:
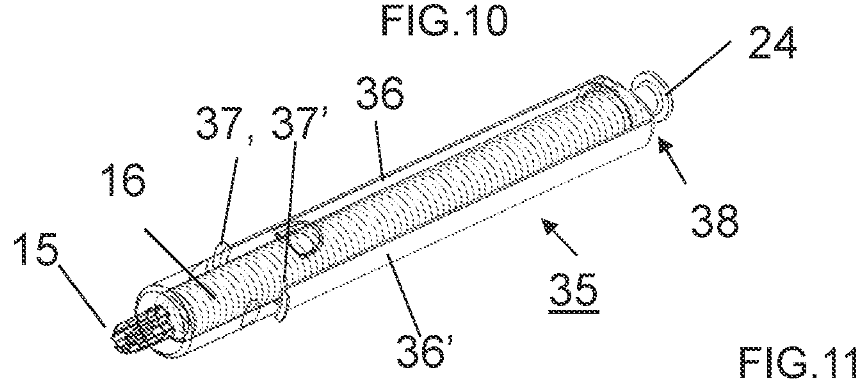
FIG. 11 illustrates a perspective view of a metal rod supporting a drive spring of the plunger rod and a signal generating element informing a user when the injection is completed.
Figure 12:
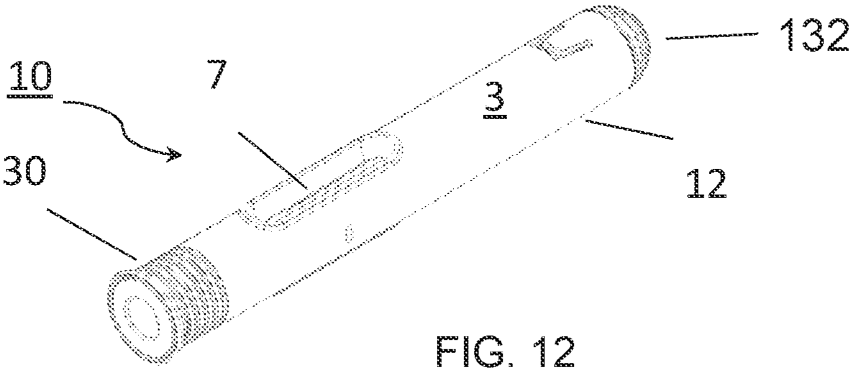
FIG. 12 illustrates a perspective view of a fully assembled medicament delivery device with an inserted pre-filled medicament container (not visible) and ready for a transportation.

Additionally, the medicament delivery device may be equipped with a signal-generating member 35, as illustrated in FIG. 11, adapted to generate an audible and/or tactile and/or visible injection confirmation signal upon a performed medicament delivery. The medicament delivery confirmation signal is generated when the drive mechanism 2 changes state from a pre-tensioned state, wherein the first drive spring 16 is pre-tensioned within the plunger rod 15, and the plunger rod 15 is engaged to the tubular body 13, to a released state, wherein the plunger rod 15 is completely released from the tubular body 13 and is no longer in contact with the signal generating member 35. In the pre-tensioned state, the plunger rod 15 is locked to the tubular body 13 by the extensions 26 on the flexible arms 6 extending radially inwards toward the central axis A and engaging the two corresponding opposite recesses 25 onto the plunger rod 15. In the release state, after the rotational member 14 is turned about the axis A by the activator 21 of about 35°, the extensions 26 of the arms 6 move out of the plunger rod 15 recesses 25 thus realising the axial movement of the plunger rod 15 in the proximal direction for the medicament delivery.

FIG. 11 is a perspective view of the signal generating member 35 in relation to the plunger rod 15 and the first resilient member 16. In the illustrated embodiment, the signal generating member 35 is an elongated u-bracket 35 adapted to enclose at least a part of the plunger rod 15 and the first resilient member 16. The signal-generating member 35 comprises two support members 37, 37' are adapted to rest on an annular surface on the proximal end 131 of the tubular body 13 when the drive mechanism 2 is in a pre-tensioned state. The proximal ends of the arms 36, 36' are provided with the angled support members 37, 37' extending in essentially radially outwards with regard to a longitudinal axis of the u-bracket 35 with is the central axis A of the injector 10.

When the drive mechanism 2 is in the pre-tensioned state, the distal end of the u-bracket 35 is arranged at a predetermined distance from an inner distal surface of a tubular interior of the distal end 132 of the support body 1. When the drive mechanism 2 is in the released state, the distal end wall 38 of the u-bracket 35 meets the distal surface of the interior the distal end 132 of the support structure 1. The audible and/or tactile and/or visible confirmation signal is generated when the distal end wall 38 of the u-bracket 35 of the signal-generating member hits and contacts the inner distal surface of the tubular body 13 distal end 132 by a remaining force exerted by the first drive spring 16. Thus, during the delivery procedure, when the distal end of the plunger rod 15 passes by the supporting members 37, 37', the arms 36, 36' with the support members 37, 37' are released and allowed to move in a radial inward direction, due to a pre-tension of the arms 36, 36', enabling the u-bracket 35 move distally and the signal, typically an audible sound and/or a visual signal and/or a tactile signal is generated, when the u-bracket 110 hits the distal end of the tubular body 13. In the pre-injection state, the u-bracket 35 is arranged such that the arms 36, 36' are positioned in a space along the plunger rod 15 between the plunger rod 15 and the tubular body 13 enclosing the plunger rod 15. The support members 37, 37' have an extension in the radial outward direction that exceeds the radial extension of the space between the plunger rod 15 and the inner wall of the tubular body 13 to secure that the signal generating member 35 is not released prior the plunger rod 15 has moved away from between the arms 36, 36'. Alternatively, the outer distal surface of the distal transversal end wall 38 may further have a protrusion (not illustrated), adapted to be guided through an opening, typically a through hole (also not illustrated) of the distal end 132 of the support structure 1 and extends distally a predetermined distance over the outer surface of the distal end 132. In an exemplary embodiment of the present disclosure, the distally extending protrusion might have a bright and/or different colour than the rest of the device 10 for generating a visual signal. Thus, such protrusion will enable both a tactile and the visual signal, when the u-bracket 35 hits the distal end 132 of the support structure 1.

It is however to be understood that embodiments described above and shown in the drawings are to be regarded only as non-limiting examples of the present disclosure and that may be modified within the scope of the appended patent claims.

The invention claimed is:

1. An elongated support structure for supporting a distal end of a medicament container in a medicament delivery device, the support structure comprises:

a tubular body having an inner dimension and an outer dimension, a longitudinal axis, a distal end and a proximal end;

at least one first flexible element arranged at the proximal end of the tubular body and having a same outer dimension and a same inner dimension as the tubular body; and a rotational member positioned on an outer circumferential surface of the tubular body, wherein the at least one first flexible element is provided with a contact member which is situated on an outer surface of the at least one first flexible element, and which outer radial dimension extends over the at least one first flexible element outer dimension enlarging a contact area of the at least one first flexible element, wherein the outer surface faces away from the longitudinal axis, and wherein the contact member is arranged to contact the distal end of the medicament container, wherein the rotational member includes a recess configured to receive and guide the contact member along the longitudinal axis, and wherein the at least one first flexible element is configured to be guided by the contact member to flex inwardly.

2. The support structure according to claim 1, wherein the at least one first flexible element comprises a first surface inclined in relation to the longitudinal axis and facing in a proximal direction.

3. The support structure according to claim 2, wherein the contact member comprises a second surface extending in an inclined direction in relation to the longitudinal axis and facing in the proximal direction.

4. The support structure according to claim 3, wherein the first surface and the second surface are situated at a same angle in relation to the longitudinal axis.

5. The support structure according to claim 3, wherein the first surface and the second surface are inclined at different angles to the longitudinal axis.

6. The support structure according to claim 1, wherein the at least one first flexible element is able to flex radially relative to the longitudinal axis when brought in contact with the medicament container distal end surface/flange.

7. The support structure according to claim 1, further comprising a second flexible element identical in shape and dimension to the at least one first flexible element and extending in a direction along the longitudinal axis from the tubular body proximal end opposite to the at least one first flexible element.

8. The support structure according to claim 1, wherein the contact member has one of a rectangular and a semi-spherical shape.

9. A drive mechanism for activating an elongated medicament delivery device having a longitudinal axis and comprising a medicament container with a proximal end and a distal end, the drive mechanism comprising:

a plunger rod for acting on the medicament container for delivery of a medicament;

a pre-tensioned drive spring inserted into the plunger rod for moving the plunger rod in a proximal direction when the plunger rod is been released;

a support structure accommodating the plunger rod with the drive spring inside and supporting on the outer surface; and an activator movable axially for interaction with the rotational member for activation of the medicament delivery device, wherein the support structure is according to claim 1.

10. A medicament delivery device comprising:

an elongated housing having a proximal end and a distal end;

a medicament container accommodated into the housing and having a proximal end and a distal end;

a plunger rod for acting on the distal end of the medicament container and driven by a drive spring;

the support structure of claim 1 with supports on its outer surface; and an axially movable activator for the medicament delivery device inserted into the housing for interacting with the rotational member.

11. The medicament delivery device according to claim 10, wherein the distal end of the support structure forms the distal end of the medicament delivery device and wherein the support structure is inserted in the distal end of the housing.

12. The medicament delivery device according to claim 10, further comprising a medicament delivery member and wherein the axially movable activator is a medicament delivery member guard, comprising a guard spring biasing the medicament delivery member guard in an extended position from the proximal end of the housing.

13. The medicament delivery device according to claim 12, wherein the medicament delivery device is an auto-injector and the medicament delivery member is an injection needle, wherein the medicament delivery device includes a protective cap comprising a needle shield remover for removal of a needle shield form the injection needle upon removal of the protective cap.

14. The medicament delivery device according to claim 13, wherein the auto-injector is a single-dose disposable injector.

15. A method of assembling the medicament delivery device according to claim 10, characterized by the steps of:

a) inserting a medicament delivery member shield remover into a protective cap;

b) inserting a spring for the activator and the activator into a central axial opening of the housing from a proximal end;

c) putting the protective cap onto a proximal end of the activator forming a first sub-assembly;

d) inserting the drive spring into the plunger rod and together into a central axial opening of the support structure; the support structure having the tubular body and the at least one first flexible element arranged at the proximal end of the tubular body; and e) placing the rotational member onto the support structure and rotating the rotational member to lock drive mechanism components together, forming a second sub-assembly, wherein providing on the at least one first flexible element the contact member situated on an outer surface of the at least one first flexible element, with the outer surface facing away from the longitudinal axis, with a proximal surface extending in a radial direction over a contact surface of the at least one first flexible element and arranged to contact the distal end of the medicament container, when inserted between the first sub-assembly and the second sub-assembly and ensuring that the first flexible element is flexing outwards relative to the longitudinal axis.

16. The method of assembling the medicament delivery device according to claim 15, further comprises the steps of:

f) inserting the medicament container into the first sub-assembly of the medicament delivery device according to steps a)-c) from the distal end of the housing; and g) inserting the drive mechanism as the second sub-assembly assembled in steps d)-e) thereafter from the distal end into the housing so that the at least one first flexible element contacts the distal end of the inserted medicament container, preventing axial movement of the medicament container.

17. A drive mechanism for operatively engaging a medicament container in a medicament delivery device, where the drive mechanism comprises:

a tubular support structure having a tubular body;

a tubular hollow plunger rod positioned within and axially slidable relative to the tubular support structure;

a compressed drive spring positioned partially within the plunger rod; and a rotational member positioned on an outer circumferential surface of the tubular body such and that rotates from a first position to a second position, where when the rotational member is in the second position the drive spring decompresses to move the plunger rod proximally relative to the tubular support structure, wherein the tubular support structure has an inner dimension and an outer dimension, a longitudinal axis, a distal end and a proximal end and two first flexible elements arranged at the proximal end of the tubular body and having an outer dimension and an inner dimension equal to the outer and the inner dimensions of the tubular body, wherein each flexible element is provided with a contact member which protrudes radially outward from an outer surface of the flexible element enlarging a contact area of each flexible element, wherein the outer surface of each flexible element faces away from the longitudinal axis, wherein each contact member is configured to contact a distal end of the medicament container, wherein the rotational member includes a recess configured to receive and guide the contact member along the longitudinal axis, and wherein each flexible element is configured to be guided by the contact member to flex inwardly.

18. The drive mechanism of claim 17, wherein each flexible element comprises a first surface inclined in relation to the longitudinal axis and facing in a proximal direction, wherein each contact member comprises a second surface that extends in an inclined direction in relation to the longitudinal axis and faces in the proximal direction, and wherein the first surface and the second surface are situated at a same angle in relation to the longitudinal axis.

19. The drive mechanism of claim 18, wherein the first surface and the second surface are inclined at different angles to the longitudinal axis and both flexible elements flex radially relative to the longitudinal axis when brought in contact with the distal end of the medicament container.

20. The drive mechanism of claim 17, wherein a distal end of the tubular support structure is configured to close and form a distal end of the medicament delivery device when the drive mechanism is inserted into a distal end of a medicament delivery device housing.

* * * * *